United States Patent [19]

Gamow et al.

[11] Patent Number: 5,367,790
[45] Date of Patent: Nov. 29, 1994

[54] SHOE AND FOOT PROSTHESIS WITH A COUPLED SPRING SYSTEM

[76] Inventors: Rustem I. Gamow, 9 Canon Park, Boulder, Colo. 80302; Hugh M. Herr, 93 Magnolia Dr., Holtwood, Pa. 17532

[21] Appl. No.: 47,872

[22] Filed: Apr. 15, 1993

Related U.S. Application Data

[63] Continuation of Ser. No. 726,891, Jul. 8, 1991, abandoned.

[51] Int. Cl.$^5$ .................... A43B 13/28; A61F 2/66
[52] U.S. Cl. ........................ 36/27; 36/7.8; 623/55
[58] Field of Search ............ 36/27, 28, 7.8, 38, 36/37; 623/55

[56] References Cited

U.S. PATENT DOCUMENTS

| | | | |
|---|---|---|---|
| 75,900 | 3/1868 | Hale et al. | 36/28 |
| 324,065 | 8/1885 | Andrews | 36/37 |
| 337,146 | 3/1886 | Gluecksmann | 36/7.8 |
| 413,693 | 10/1889 | Walker | 36/7.8 X |
| 427,136 | 5/1890 | Walker | 36/7.8 X |
| 733,167 | 7/1903 | Denton | 36/37 X |
| 1,352,865 | 9/1920 | Augestad | 36/27 |
| 1,726,028 | 8/1929 | Keller | 36/7.8 |
| 2,413,545 | 12/1946 | Cordi | 36/7.8 X |
| 4,091,472 | 5/1978 | Daher et al. | 623/55 |
| 4,360,978 | 11/1982 | Simpkins | 36/7.8 X |
| 4,566,206 | 1/1986 | Weber | 36/27 X |
| 4,652,266 | 5/1987 | Truesdell et al. | |
| 4,822,363 | 4/1989 | Phillips et al. | |
| 4,892,554 | 1/1990 | Robinson et al. | |
| 4,910,885 | 3/1990 | Hsieh | 36/38 X |
| 4,941,273 | 7/1990 | Gross et al. | |
| 4,942,046 | 1/1985 | Kosova et al. | |

FOREIGN PATENT DOCUMENTS

| | | | |
|---|---|---|---|
| 0103041 | 3/1984 | European Pat. Off. | 36/27 |
| 0472735 | 12/1916 | France | 36/37 |
| 1227420 | 8/1960 | France | 36/37 |
| 2507066 | 12/1982 | France | 36/27 |
| 3415705 | 10/1985 | Germany | 36/28 |
| 2200030 | 7/1988 | United Kingdom | 36/27 |

OTHER PUBLICATIONS

K. J. Fisher "Advanced Composites Step into Athletic Shoes," *Advanced Composites,* May/Jun. 1991, pp. 32–35.
Product Literature from LA Gear regarding the Catapult Shoe Design.
Discovery, Oct. 1989 pp. 77–83, Kunzig.

*Primary Examiner*—Steven N. Meyers
*Assistant Examiner*—Ted Kavanaugh
*Attorney, Agent, or Firm*—Greenlee and Winner

[57] ABSTRACT

The invention relates to a sole system for use especially with an athletic shoe or prosthesis. The sole includes a coupled spring configuration that forms a collapsible, longitudinal arch to permit maximum storage and release of energy during the running cycle.

7 Claims, 5 Drawing Sheets

SHOE AND FOOT PROSTHESIS WITH A COUPLED SPRING SYSTEM

This is a continuation of copending application(s) Ser. No. 07/726,891, filed Jul. 8, 1991, now abandoned.

TECHNICAL FIELD

The invention relates to a sole system for use especially with an athletic shoe or prosthesis. The sole includes a coupled spring configuration that forms a collapsible, longitudinal arch to permit maximum storage and release of energy during the running cycle.

BACKGROUND OF THE INVENTION

Developers of athletic shoes are confronted with the problem of storing energy in the sole of the shoe and releasing the energy in a manner which improves the efficiency of the locomotor system to propel the body forward.

Many examples of running shoes exist; however, very few, if any, have been embraced by runners and foot specialists. Studies of the dynamics of the human foot reveal that the longitudinal arch of a human foot, with its numerous joints and ligaments, is capable of returning 70% of the energy put into it and that it is far more efficient than the soles of the best existing running shoes. See Discovery, October 1989 (pp. 77-83). If runners could run with bare feet, many would prefer to do so. However, impact forces are too great and the foot needs protection, especially on hard surfaces.

Athletic shoes have been proposed which have not been entirely satisfactory in that either the stored energy of heel-strike is not transmitted to the runner in the most effective manner to maximize running efficiency or the energy which enhances running efficiency is stored during the push-off period of the running cycle, thereby, impact energy losses are not used. These problems are overcome by the present invention. The inventors hereof have discovered that for heel-toe running, energy should be stored in the sole of the shoe at heel-strike and then, in turn, this stored energy should be released at a critical time and in a particular manner to enhance toe-off propulsion.

While purporting to provide for maximum performance, the latest technology in running shoes fails to achieve the ultimate design which permits maximum storage and return of energy for a variety of running modes ranging from heel-toe running (long-distance) to flat-footed running or toe running (sprinting).

U.S. Pat. No. 4,941,273 (Gross) discloses an athletic shoe having a sole arrangement which contains an elastic band extending through a longitudinal passageway in the mid-sole. The purpose of this device is to create an artificial tendon by facilitating the storage and release of strain energy created during the running cycle. However, because of the position of the elastic band relative to the sole plate, the energy stored at heel strike is not transmitted to the toe to enhance toe-off propulsion.

On the other hand, U.S. Pat. No. 4,492,046 (Kosova) describes a sole of a running shoe having a wire spring. The wire spring serves to bias the anterior portion of the sole from the heel (back of the shoe) forward to the arch region, separating the anterior of the sole into upper and lower portions. The objective of this device is to enhance the runner's performance by reducing impact at heel-strike and launching the runner forward into a comfortable stride. Unfortunately, this device in practice provides energy return immediately at heel-lift, precluding storage of energy which could otherwise be used to propel the runner forward as claimed in the disclosed invention.

The latest commercial running shoes fail to completely address the desired attributes of a properly designed running shoe. For example, several attempts at returning energy only provide a heel-lift assist, permitting little forward propulsion. Others, although claiming to facilitate propulsion at toe-off, are incapable of storing the kinetic (muscle-generated) and potential energies of the runner at heel-strike, allowing a fraction of these energies to be lost to heat and to internal joint resistance (internal damping).

Similar challenges have confronted developers of lower-extremity prosthetic limbs. While it has effected substantial improvements, prosthetic research has so far focused almost exclusively on simulation or duplication of a natural foot in an attempt to provide the amputee with a normal gait and a greater degree of comfort. See U.S. Pat. No. 4,652,266 (Truesdell). A recent improvement emerging from prosthetic research is the College Park Foot design disclosed in U.S. Pat. No. 4,892,554 (Robinson). This design describes a prosthetic foot having an ankle member, a heel member and an elongated metatarsal-toe member coupled to each other for relative pivotal movements. The toe member is partially bifurcated at its forward end to provide independently flexible toe sections at the inner and outer sides of the foot. This design thus represents a three-point balance system achieving a stable support matching that of a natural foot.

One notable exception is the device disclosed in U.S. Pat. No. 4,822,363 (Phillips). This patent describes a composite prosthetic foot having a leg portion, a foot portion and a heel portion all rigidly joined and all three provided with substantial elasticity to allow return of energy absorbed and permit the amputee to engage in sports such as running and playing tennis. Understandably, this design has met with general approval from amputees who are sport enthusiasts, and at the same time enjoyed commercial success.

Like its running shoe counterpart, the above disclosed invention does not contain a mechanism whereby energy absorbed at heel-strike can be stored and later released at the critical moment to create forward propulsion. In addition, the device does not have significant means for storing energy upon impact for the flat-footed runner, i.e., no real longitudinal arch.

The present invention represents a significant improvement over the prior art. Included in the design of the present invention is a collapsible, longitudinal arch formed by coupled springs which operates to delay the release of absorbed energy until toe-lift, thereby propelling the runner forward into a comfortable stride. The purpose of the present invention is to minimize energy losses during the impact phase and to use these energies to improve the runner's overall efficiency. The design can be incorporated into either a shoe for use with a natural foot or a foot prosthesis specially fabricated for amputees wishing to participate in athletic activities. Moreover, the present invention maximizes the runner's performance in all running modes including heel-toe running, sprinting and running flat-footed.

SUMMARY OF THE INVENTION

This invention comprises a sole system for attachment to the underside of a foot comprising a plurality of coupled springs for absorbing the energy of impact of the heel of said foot against a surface and releasing said energy after sufficient delay to allow said foot to roll forward, whereby said released energy provides a horizontal and vertical component of force to the front portion of said foot to enhance forward lift of said foot.

The coupled springs may consist of a plurality (two or more) springs positioned with respect to each other such that energy absorbed by a first spring or springs is transferred to one or more additional springs and released by said additional spring or springs. The first spring or springs are positioned beneath said foot so as to absorb energy from impact of the foot against a surface (referred to herein as "heel-strike"), and release the absorbed energy in such a way as to allow at least a portion of said energy to be absorbed by a second spring or springs. Said second spring or springs release the energy against the underside of the front portion of the foot, i.e. at or near the ball of the foot, to provide both an upward and a forward component of force to propel the foot forward and upward (referred to herein as "toe-off").

By this arrangement sufficient delay is provided between absorption of energy from the heel-strike and release of energy back to the front part of the foot to allow the foot to roll forward in a normal walking or running gait before the energy is released to enhance toe-off propulsion.

The first spring or springs may be directly attached to the second spring or springs, or there may be intervening springs or rigid members between them. Any arrangement of springs and other members may be used so long as energy is absorbed at heel-strike, delayed to allow rolling forward of the foot, and transferred to the front portion of the foot for release.

This invention also provides a sole system comprising a collapsible arch preferably positioned forward from the natural longitudinal arch so that the apex of the said collapsible arch lies between the apex or transverse axis of the natural longitudinal arch and the natural axis of rotation of the foot at the ball of the foot, or so that the apex of the said collapsible arch lies at said axis of rotation of the foot such that energy is stored by said arch upon impact of the foot against a surface and released to propel the foot away from said surface.

When said coupled springs are combined to form a collapsible arch, energy stored by the impact of the heel against a surface will be stored and released at the axis of rotation of the foot so as to move the foot upward and forward.

The preferred embodiment of this invention provides a spring configuration to be used in the sole of a shoe or in a prosthetic foot, capable of storing energy upon impact of the foot with a running surface, and releasing this energy at the toe-off phase of the running cycle to enhance running efficiency. To attain this, the preferred embodiment of the present invention provides a spring configuration made of suitable energy-absorbing material, e.g., a carbon fiber composite or other suitable materials known to the art having non-plastic properties.

The preferred embodiment of this invention consists of a sole system comprising two coupled springs, a heel spring and a sole spring. The two springs together form a longitudinal arch when in an equilibrium or relaxed state. During heel-toe running, the heel spring compresses during heel impact. This stored energy is then, in turn, transferred to the sole spring which enhances toe-off propulsion. The compression of the heel spring also reduces impact forces on the body during heel-strike.

The exact nature of this invention as well as other objects and advantages thereof will be readily apparent from consideration of the following specification relating to the drawings.

BRIEF DESCRIPTION OF THE DRAWINGS

FIG. 4 shows the spring configuration at the instant of heel-strike.

FIG. 5 shows the spring configuration at mid-stance when the heel spring is fully compressed.

FIG. 6 shows the spring configuration during heel lift-off.

FIG. 7 shows the spring configuration right before toe-off.

FIG. 8 shows the spring configuration at the instant after toe-off.

DETAILED DESCRIPTION OF THE PREFERRED EMBODIMENTS

The following principles govern the improved sole system of this invention:

1. The system should not inhibit the natural movements of the biological locomotor system, i.e. the foot and ankle must be able to bend freely. Thus, the sole spring of this invention should bend with the foot.

2. The system should store energy upon impact of the shoe with the running surface (during the impact phase of the running cycle), regardless of what portion of the foot strikes the surface initially. A longitudinal arch configuration satisfies this principle.

3. Stored energy should be released to enhance straightening of the foot at toe-off. Because the motion of straightening the foot at toe-off is less efficient than heel-lift, the stored energy of impact should be released in a manner which enhances the efficiency of the toe-off motion.

The invention consists of a sole system which comprises: a sole spring compressible about a transverse (lateral) axis positioned between and beneath the apex (transverse axis) of the natural longitudinal arch of the foot and the ball of the foot or just beneath said apex or ball of the foot; and a heel spring coupled to said sole spring and in combination therewith forming a collapsible longitudinal arch having an apex at or proximal to said axis and distal to the transverse axis or apex of the natural longitudinal arch in an equilibrium state for absorbing energy upon impact with a running surface, whereby the collapsible arch serves as a mechanism for storing and delaying energy absorbed by the heel spring at heel-strike and later releasing the same during toe-off to create a forward propulsion.

It is desirable that the sole system of this invention flex with the natural movements of the foot. Thus, the sole spring should rotate about an axis corresponding to the natural axis of rotation of the foot near the ball of the foot. It is also desirable that the axis of rotation for the heel spring (which corresponds to the apex of the longitudinal arch) be as far forward as possible to maximize energy storage and release. Thus, it is preferred that the apex of the longitudinal arch correspond to the transverse axis of rotation.

Figure 1:
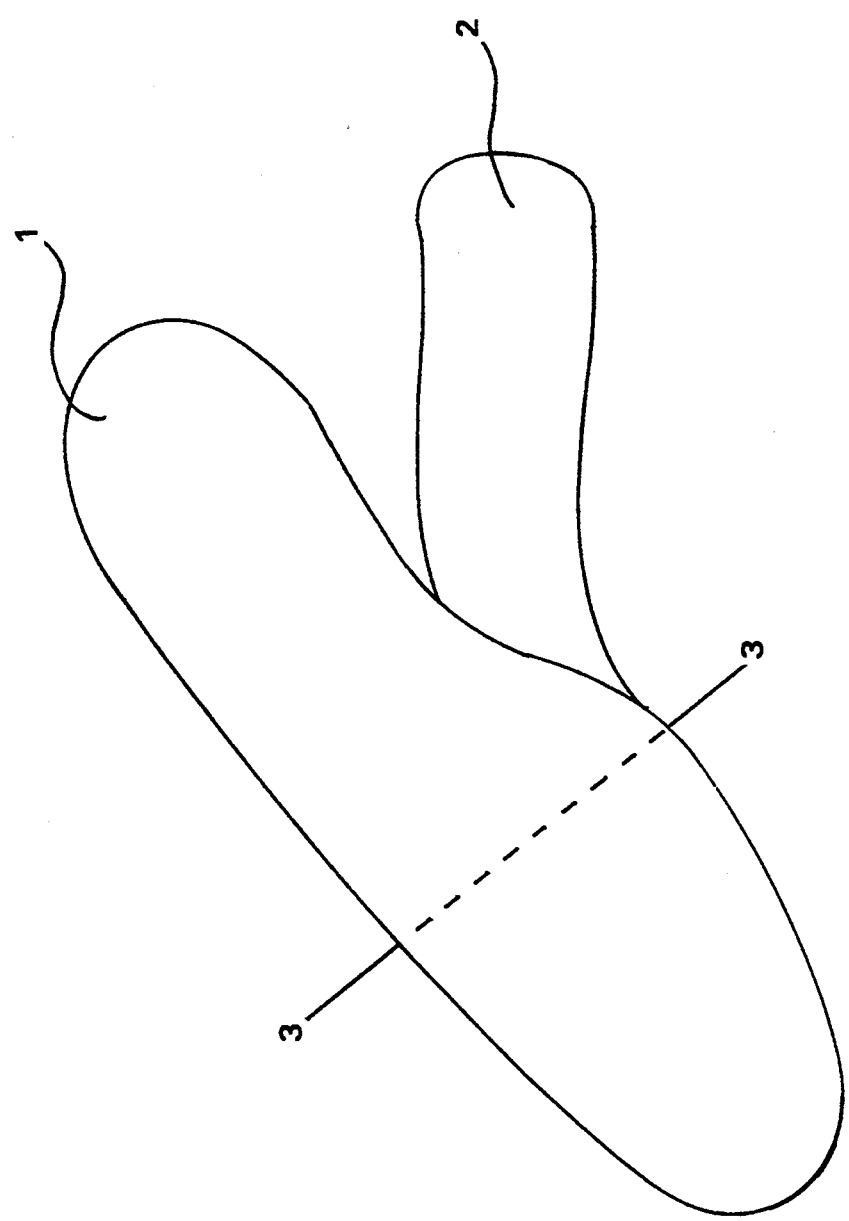
FIG. 1 shows a perspective view of the equilibrium coupled spring configuration.
Figure 2:
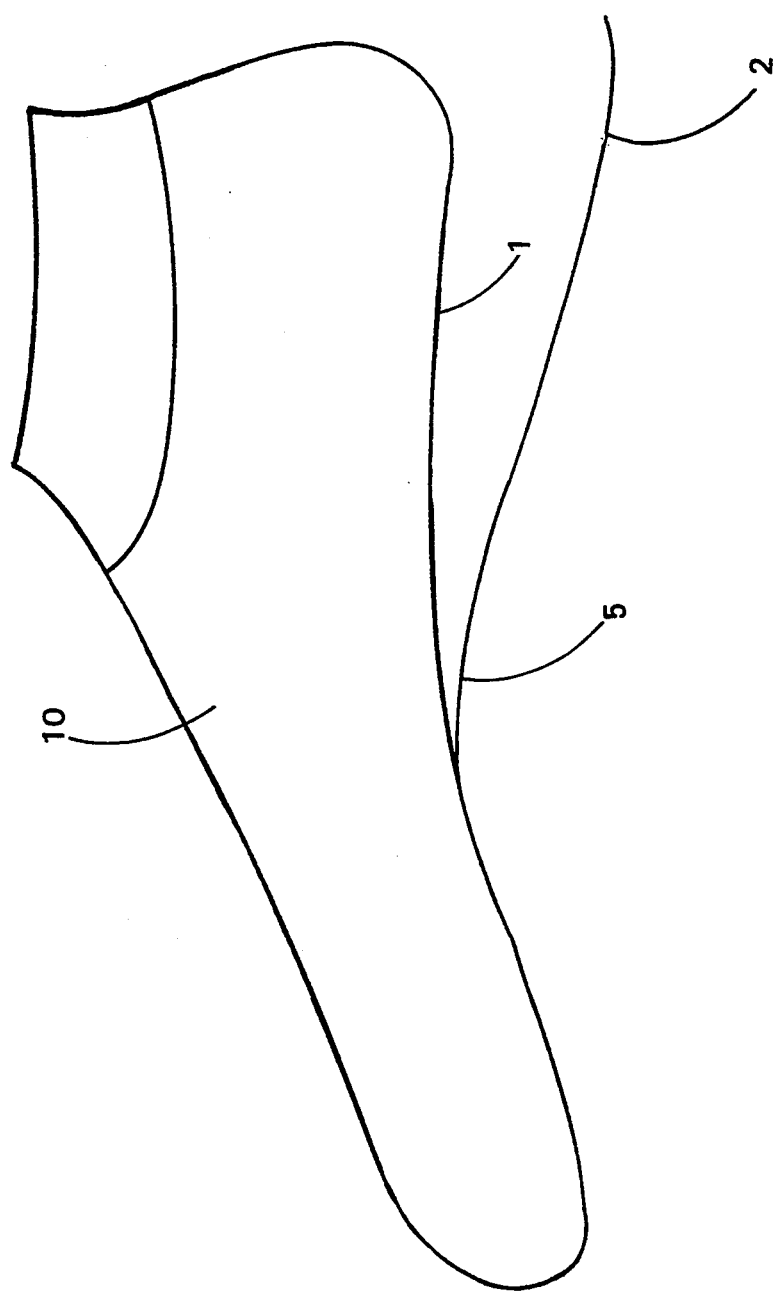
FIG. 2 shows a side view of the equilibrium coupled spring configuration including the upper shoe or the cosmetic cover for the foot prosthesis.

FIGS. 1 and 2 show a sole arrangement according to the preferred embodiment of the invention. FIG. 2 also shows the sole arrangement fitted to the shoe upper or the cosmetic cover of the foot prosthesis 10. It should be understood that in use the spring would be inside the prosthetic cover or shoe sole. The sole arrangement comprises a sole spring 1, and a heel spring 2. The sole spring 1 and the heel spring 2, independently of each other, compress about a transverse axis approximately beneath the distal bases of the metatarsals (commonly known as the ball of the foot)i.e., at a point approximately $\frac{2}{3}$ of the length of the sole spring from the end thereof. The sole spring 1 extends the full length and width of the underside of the foot, while the heel spring 2 extends from the heel forward to the transverse axis 3.

The sole spring 1 and the heel spring 2 are coupled and form a collapsible, longitudinal arch 5, (the apex of which preferably corresponds to the transverse axis 3 near the ball of the foot or is located proximal to said axis between the ball of the foot and the apex of the natural longitudinal arch).

Figure 3:
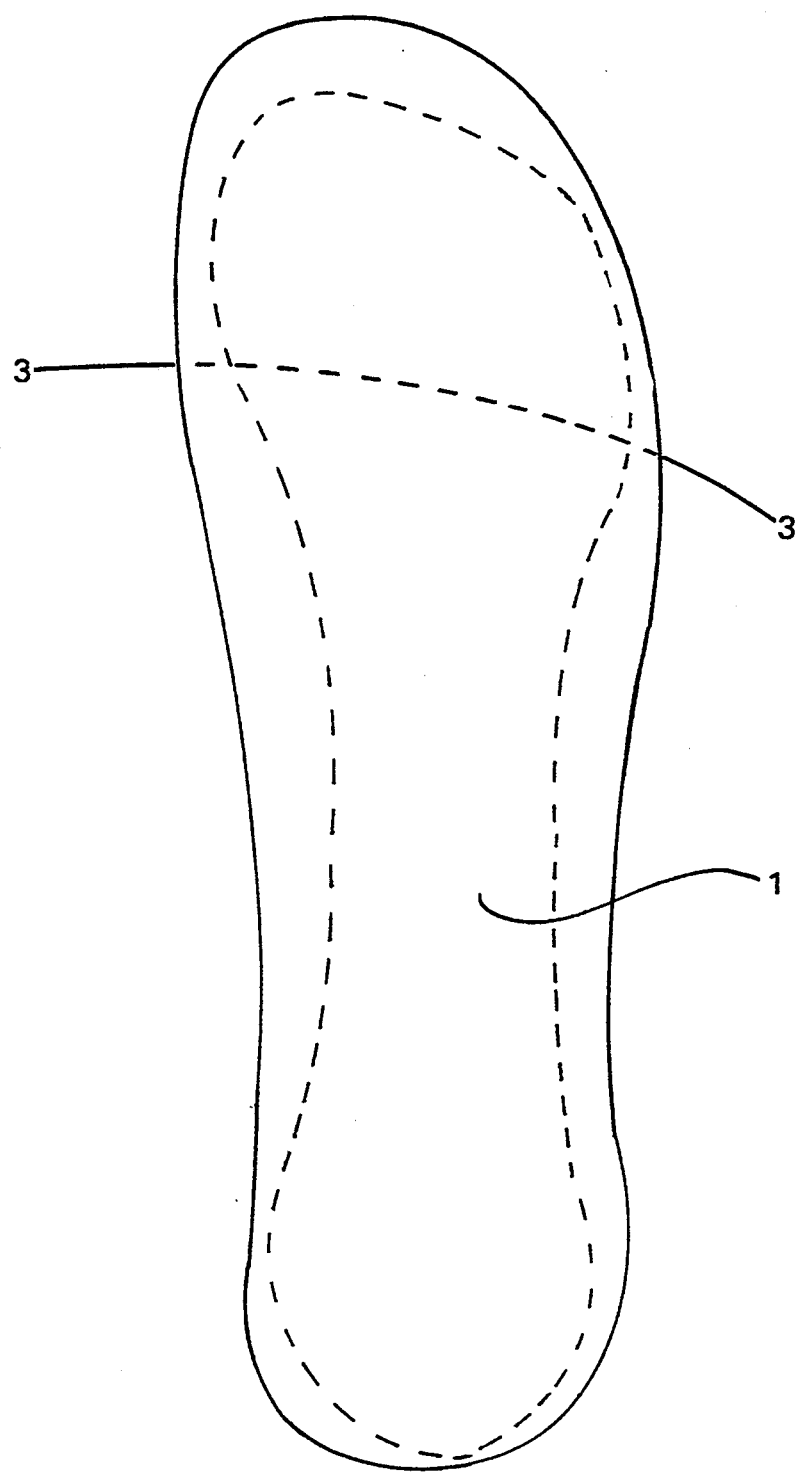
FIG. 3 shows a top view of the coupled spring system in its equilibrium configuration excluding the upper shoe and other sole components.

FIG. 3 shows the sole spring 1 with the transverse axis 3 relative thereto. FIGS. 4 through 8 show a sequence of spring configurations corresponding to various phases of the heel-toe running cycle, with respect to the transverse axis 3 and the running surface 7.

Figure 4:
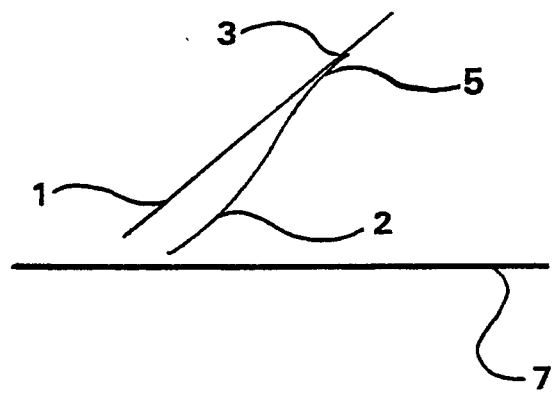
FIGS. 4 through 8 show a sequence of spring configurations with respect to the axis of transverse rotation and the running surface.
Figure 5:
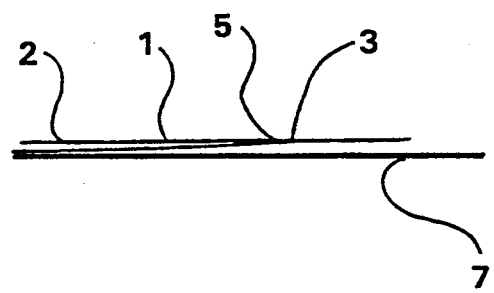

FIG. 4 shows the heel spring 2 being compressed about axis 3 during heel-strike while FIG. 5 shows the sole spring 1, the heel spring 2 and the arch 5 fully compressed at mid-stance. As the body passes over the foot and the weight of the runner is transferred toward the forefoot, the compressed heel spring 2 begins to expand, causing the sole spring 1 to compress about transverse axis 3. The compressed sole spring, in turn, expands to enhance toe-off propulsion. In effect, the energy at heel-strike is stored in the spring configuration and energy release delayed by means of the collapsible arch until the toe-off phase at which time the sole spring 1 transmits the energy to the runner in a manner which enhances toe-off propulsion.

Figure 6:
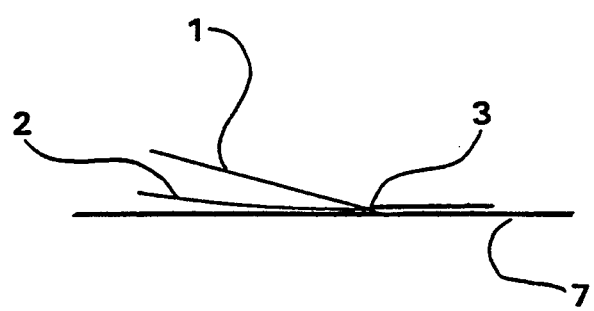
Figure 7:
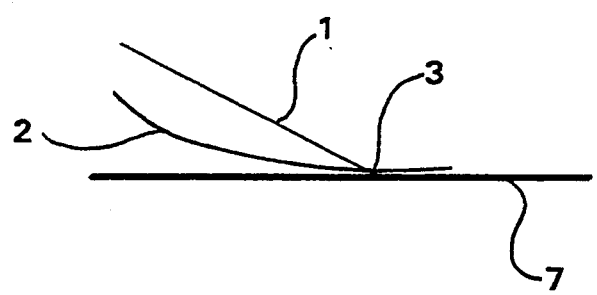
Figure 8:
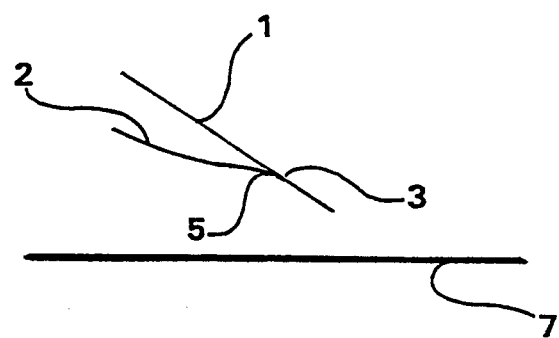

FIG. 6 illustrates the transfer of energy from the heel spring 2 to the sole spring 1. FIG. 7 demonstrates the spring configuration at the instant before the toe-off phase begins. FIG. 8 represents the position of the sole immediately after toe-off showing the final approximate direction or angle of propulsion. Thus, the coupled spring system introduced by the present invention operates to maximize the storage, hence, the return of energy at the critical moment at toe-off to enhance the user's speed and endurance while running.

The spring system of this invention can be fabricated as one piece having the forked configuration shown in the figures, or as several pieces attached by suitable attachment means to form the depicted configuration.

Obviously, many modifications and variations of the present invention are possible in the light of the above principles and will be evident to those of ordinary skill in the art. For example, the springs may be constructed with an energy absorbing material wedge, wholly or partly solid. Or, the springs may be fabricated as a fluid-filled, coupled reservoir whereby fluid such as air, water or gel from the reservoir under the heel is propelled via a one way valve into an expandable chamber under the ball of the foot to provide lift-off energy at toe-off. It is to be understood, however, the coupled reservoir is effective only in heel-toe running.

The strength or stiffness of the sole spring should be less than that of the heel spring so as to permit effective transfer of energy from the heel spring to the sole spring.

The width, length and shape of the springs can be adjusted as is well known in the art of athletic shoes to reduce excessive movements in the joints of the locomotor system causing over pronation and/or over supination of the foot. For example, rounding the lateral-posterior edge of the sole and/or adjusting the stiffness of this portion helps reduce over-pronation of the foot.

Additionally, the width, length and shape of the springs can be altered so that the device interfaces effectively with the anatomical curves of the human foot.

Still further, the distal portion of the sole spring can be curved so the system rolls smoothly on the running surface during the toe-off phase.

In a further improved embodiment of this invention, the portion of the sole spring distal to the transverse axis thereof can be angled downward in the equilibrium position, effectively raising the height of the collapsible arch apex configuration without raising the heel height. The longitudinal arch will collapse as a result of heel collision and forefoot collision with the running surface.

The term "coupled spring" herein includes the case where not only the release of a first spring compresses an adjacent or linked spring when the device is in use, but also the case where the compression of the first spring also compresses a second adjacent or linked spring. Thus in one embodiment of this invention, the pressure of heel-strike against the heel spring also causes absorption of energy by a forefoot spring which is released at toe-off to enhance toe-off propulsion.

The spring configuration can be either an integral part of the sole or affixed to the bottom of a sole of a shoe or prosthesis. Additional elements, e.g., wedges filled with air or gel, may be employed to regulate the spring stiffness to meet various requirements and conditions for the benefit of the person using the device.

It is therefore to be understood that within the scope of the appended claims, the invention may be practiced in ways other than as specifically described herein.

We claim:

1. A sole system which is part of a shoe which comprises: a sole spring having a heel end and a toe end compressible about a transverse axis positioned at a point approximately $\frac{2}{3}$ of the length of the sole spring from the heel end thereof; and a heel spring having a curved portion coupled to said sole spring, and in combination with said sole spring forming a collapsible longitudinal arch, said heel spring having an axis of rotation at the apex of said longitudinal arch, and wherein the stiffness of the sole spring is relatively less than that of the heel spring.

2. The sole system of claim 1 wherein the heel spring and the sole spring are of carbon fiber composite.

3. The sole system of claim 1 wherein the sole spring distal to the transverse axis is angled downward when the spring is in a relaxed state.

4. A shoe fitted with the sole arrangement of claim 1.

5. A prosthetic foot which comprises: a sole spring having a heel end and a toe end compressible about a transverse axis positioned at a point approximately ⅔ of the length of the sole spring from the heel end thereof; and a heel spring having a curved portion coupled to said sole spring, and in combination with said sole spring forming a collapsible longitudinal arch, said heel spring having an axis of rotation at the apex of said longitudinal arch, and wherein the stiffness of the sole spring is relatively less than that of the heel spring.

6. The prosthetic foot of claim 5 wherein the heel spring and the sole spring are of carbon fiber composite.

7. The prosthetic foot of claim 5 wherein the sole spring distal to the transverse axis thereof is angled downward when the spring is in a relaxed state.

* * * * *